(12) United States Patent
Lorant (10) Patent No.: US 7,772,004 B2
(45) Date of Patent: Aug. 10, 2010

(54) METHOD AND DEVICE FOR DETERMINING PETROLEUM CHARACTERISTICS OF GEOLOGIC SEDIMENTS

(75) Inventor: François Lorant, Thiais (FR)

(73) Assignee: Institut Francais du Petrole, Cedex (FR)

( * ) Notice: Subject to any disclaimer, the term of this patent is extended or adjusted under 35 U.S.C. 154(b) by 901 days.

(21) Appl. No.: 11/587,958

(22) PCT Filed: Apr. 15, 2005

(86) PCT No.: PCT/FR2005/000921
§ 371 (c)(1),
(2), (4) Date: Oct. 27, 2006

(87) PCT Pub. No.: WO2005/111603
PCT Pub. Date: Nov. 24, 2005

(65) Prior Publication Data
US 2008/0026471 A1     Jan. 31, 2008

(30) Foreign Application Priority Data
Apr. 28, 2004   (FR) .................................. 04 04607

(51) Int. Cl.
G01N 31/12 (2006.01)
G01N 33/24 (2006.01)

(52) U.S. Cl. ........................... 436/32; 422/68.1; 422/78; 422/80; 436/29; 436/31; 436/119; 436/120; 436/122; 436/123; 436/133; 436/134; 436/155; 436/157; 436/158; 436/160

(58) Field of Classification Search .................... 422/63, 422/67, 68.1, 78–80, 82.09; 436/25, 29, 436/31–32, 91, 119–123, 133–134, 155, 436/157–158, 160
See application file for complete search history.

(56) References Cited

U.S. PATENT DOCUMENTS 3,880,587 A * 4/1975 Szakasits et al. ............ 436/123
(Continued)

FOREIGN PATENT DOCUMENTS
EP          0 269 511        6/1988
(Continued)

OTHER PUBLICATIONS

LaCount, R. B. et al, Fuel 1987, 66, 909-913.*
(Continued)

*Primary Examiner*—Arlen Soderquist
(74) *Attorney, Agent, or Firm*—Antonelli, Terry, Stout & Kraus, LLP.

(57) ABSTRACT

The invention relates to a method allowing to determine at least one petroleum characteristic of a geologic sediment sample, wherein the sample is heated in an oxidizing atmosphere, its temperature being successively raised to a first, then to a second value, said first value below 200° C. being reached very quickly, then maintained substantially constant for a certain time, said second value ranging between 600° C. and 850° C. being reached with a temperature gradient ranging between 1 and 30° C./min, from said first value. According to the invention, the amount of $SO_2$ contained by the effluent resulting from said oxidizing heating is measured continuously, every moment of the heating period of said sample.

6 Claims, 4 Drawing Sheets

U.S. PATENT DOCUMENTS

| | | | |
|---|---|---|---|
| 3,953,171 A * | 4/1976 | Espitalie et al. | 436/32 |
| 4,153,415 A * | 5/1979 | Espitalie et al. | 436/31 |
| 4,213,763 A | 7/1980 | Madec et al. | |
| 4,229,181 A * | 10/1980 | Espitalie et al. | 436/31 |
| 4,352,673 A * | 10/1982 | Espitalie et al. | 436/145 |
| 4,824,790 A * | 4/1989 | Carangelo et al. | 436/157 |
| 4,837,158 A * | 6/1989 | Toulhoat et al. | 436/37 |
| 4,845,040 A | 7/1989 | Moon et al. | |
| 5,786,225 A * | 7/1998 | Lafargue et al. | 436/147 |
| 5,811,308 A * | 9/1998 | Espitalie et al. | 436/145 |
| 6,254,828 B1 * | 7/2001 | LaCount | 422/78 |

FOREIGN PATENT DOCUMENTS

| | | |
|---|---|---|
| EP | 0767375 | 4/1997 |
| FR | 2339173 | 1/1976 |
| FR | 2472754 | 12/1979 |
| WO | WO 92/19964 | 11/1992 |

OTHER PUBLICATIONS

Whelan, J. K. et al, Energy & Fuels 1988, 2, 65-73.*
Bassilakis, R. et al, Energy & fuels 1993, 7, 710-720.*
LaCount, R. B. et al, Fuel 1993, 72, 1203-1208.*
Paama, L. et al, Talanta 2000, 51, 349-357.*

* cited by examiner

METHOD AND DEVICE FOR DETERMINING PETROLEUM CHARACTERISTICS OF GEOLOGIC SEDIMENTS

FIELD OF THE INVENTION

The present invention relates to a method and to an improved device for determining at least some of the petroleum characteristics of a geologic sediment, such as for example, but not exclusively, the possibility of producing oil immediately or in the future, i.e. of being a good source rock, or of being a hydrocarbon-containing reservoir rock.

The present invention relates to an improvement to the ROCKEVAL technique (trade name registered by Institut Francais du Pétrole) and to an optimization of the measuring device used to implement the method. The prior ROCKEVAL technique is described in documents FR-2,339,173 and FR-2,472,754.

BACKGROUND OF THE INVENTION

The prior method and devices do not allow continuous measurement of the gas $SO_2$ during the heating cycle in an oxidizing atmosphere (oxidation cycle). Now, an analysis of the $SO_2$ formed during oxidation of the organic matter is essential to determine the organic sulfur and mineral sulfur contents of said organic matter. Furthermore, this analysis can be carried out on the one hand directly from a first aliquot of an organic matter sample, and on the other hand with a second aliquot of the sample after it has first been subjected to a pyrolysis cycle. Comparison of these two measurements allows quantitative characterization of the total organic sulfur in a thermally labile fraction and a thermally refractory fraction.

All this information on the sulfur contents of a kerogen type material is important for knowledge of the production potentiality of a reservoir. For example, measurement of the $SO_2$, by giving access to the organic and mineral sulfur contents of the kerogens, allows in fact to better characterize the various types of source rocks and their degree of thermal maturation, notably through determination of the labile and refractory sulfur contents. This measurement also allows to fine down the source rock oil correlations by comparison of the distribution of the sulfur and of its proportion in the oils and in the source rock pyrolysates. On a petroleum reservoir scale, the $SO_2$ measurement performed from bitumen extracted from cores allows to make a diagnosis concerning their origin and their distribution in the reservoirs (gravity segregation, biodegradation, washout, thermal cracking, etc.). Differentiation between the $SO_2$ of organic origin and the $SO_2$ from pyrite allows to distinguish the bitumen and pyrobitumen levels, therefore the reservoir levels, from the source rock levels.

SUMMARY OF THE INVENTION

The present invention thus relates to a method allowing determination of at least one petroleum characteristic of a geologic sediment sample, wherein the sample is heated in an oxidizing atmosphere, its temperature being successively raised to a first, then to a second value, said first value below 200° C. being reached very quickly, then maintained substantially constant for a certain time, said second value ranging between 600° C. and 850° C. being reached with a temperature gradient ranging between 1 and 30° C./min, from said first value. According to the invention, the amount of $SO_2$ contained in the effluent resulting from said oxidizing heating is measured continuously, every moment of the heating period of said sample.

A curve representative of said $SO_2$ amount can be drawn, and the $SO_2$ of organic origin can be distinguished from the $SO_2$ of mineral origin from said continuous measurements and from the shape of the curve.

The following two stages can be carried out:

continuous measurement of the amount of $SO_2$ contained in the effluent resulting from said oxidizing heating of part of the sample previously subjected to a pyrolysis stage in an inert atmosphere, continuous measurement of the amount of $SO_2$ contained in the effluent resulting from said oxidizing heating of another part of the sample.

The labile organic sulfur can be distinguished from the refractory organic sulfur through combined interpretation of the measurements resulting from said two stages.

The invention also relates to a device allowing determination of at least one petroleum characteristic of a geologic sediment sample placed in a boat, said device comprising a first means for heating said sample in a non-oxidizing atmosphere, means for measuring the amount of hydrocarbon products released after feeding the sample into said first heating means, a second means for heating the sample in an oxidizing atmosphere. The device comprises a cell intended for continuous measurement of the $SO_2$ every moment of the heating cycle of the second heating means.

The device can comprise a first set of cells intended for continuous measurement of the $CO_2$ and of the CO contained in the effluent released by the first heating means and a second set of cells intended for continuous measurement of the $SO_2$, $CO_2$ and CO contained in the effluent released by the second heating means.

Said measuring cells can preferably be of infrared type.

BRIEF DESCRIPTION OF THE FIGURES

Other features and advantages of the present invention will be clear from reading the description hereafter, with reference to the accompanying figures wherein.

DETAILED DESCRIPTION

The principle of the method is described hereafter. A rock or concentrated organic matter sample is subjected to a programmed heating law, either directly in an oxidizing atmosphere or first in an inert atmosphere, then in an oxidizing gas stream, so that each analysed product release corresponds to the real temperature of the sample at the time of its production. The effluents are continuously analysed by a flame ionization detector (FID) for the hydrocarbons released during heating in an inert atmosphere, and by an infrared (IR) device for the $SO_2$ produced by oxidation of the organic matter, or decomposition of the sulfur-containing minerals, pyrite and sulfates for example. The same infrared (IR) device also allows continuous measurement of the $CO_2$ and of the CO produced by the sample when heated in an inert atmosphere and in an oxidizing atmosphere.

The various curves are then integrated and interpreted to obtain the first analysis results:

the amount of sulfur contained in the free hydrocarbons (peak OS1, FIG. 3A), the organic sulfur potential of the sample analysed (peak OS2, FIG. 3A), the mineral sulfur potential of the sample analysed (peak OS3, FIG. 3A), whose shape, intensity and position in temperature can vary depending on the nature of the minerals present in the sample analysed, notably its pyrite and sulfate content, the ratio of the amount of organic sulfur referred to as refractory to the amount of organic sulfur referred to as labile is defined from the ratio between peak TS (FIG. 3B) obtained by heating in an oxidizing atmosphere part of an organic matter sample and peak TSr (FIG. 3B) obtained by subjecting a second part of this organic matter sample successively to the first (pyrolysis in an inert atmosphere), then to the second heating means (oxidation).

Various necessary ratios derived from the new functions characterizing the sample analysed will be deduced from these base elements.

The device according to the invention is made up of an automaton performing the measurements and of a PC which controls the automaton, serves as an interface with other computers, manages the analyses, allows real-time display of the results and uses control and test softwares.

The measuring device comprises two micro-ovens, a sample changer supplying them with boats and an analysis system consisting of a flame ionization detector (FID) and of at least one infrared (IR) cell. These elements are connected to electronics and to a fluid circuit managed by the PC and by the automaton software.

Figure 1:
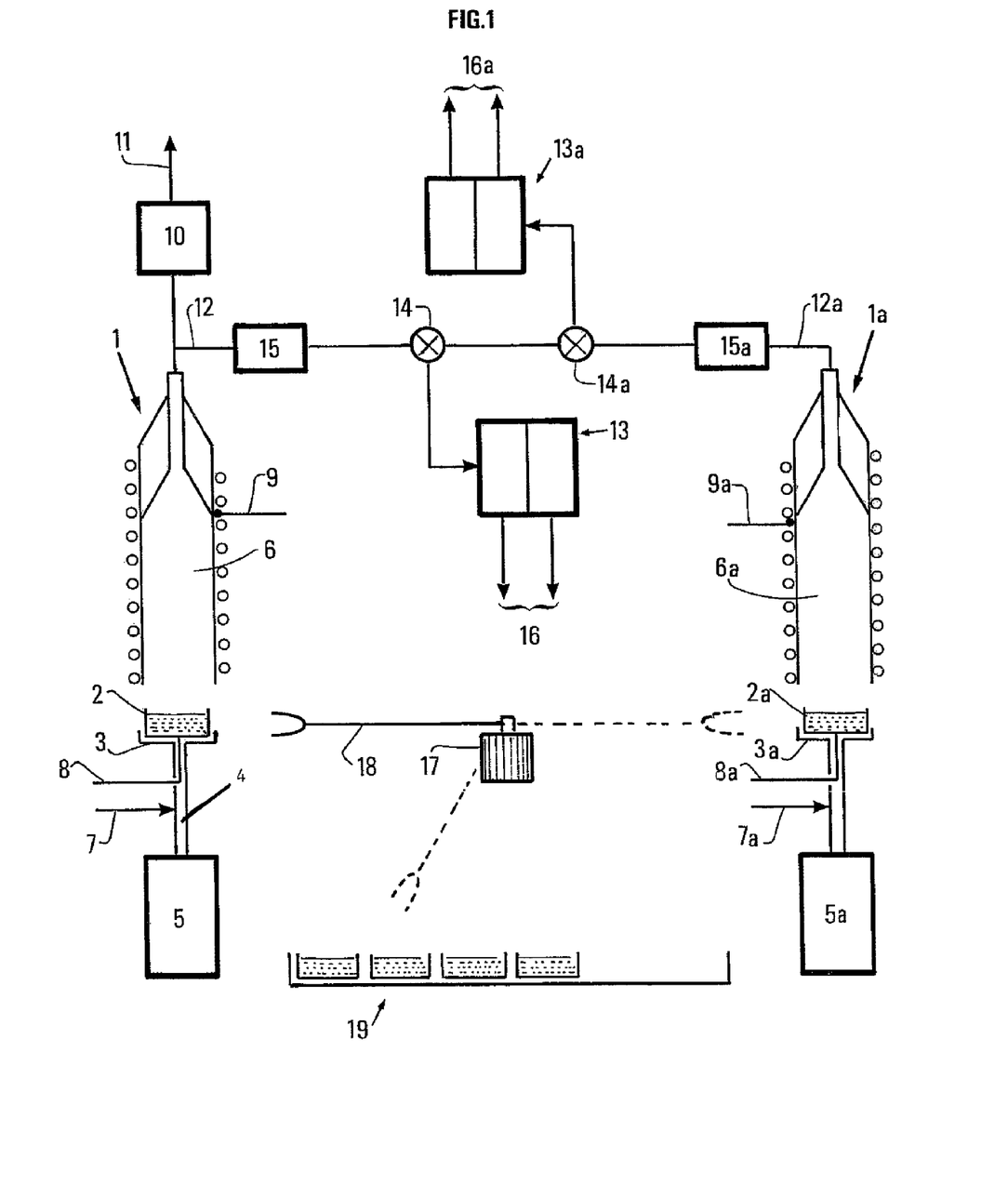
FIG. 1 is the flowsheet of the measuring device.

FIG. 1 describes the improved pyrolysis and oxidation device according to the present invention. Reference number 1 designates the heating set suited for pyrolysis of sample 2 placed in a boat 3 carried by a piston 4. Boat displacement means 5 feed the sample into the inner space 6 of the oven. The displacement means can be pneumatic, hydraulic or electric jacks. Reference number 7 shows the line delivering the carrier fluid intended to sweep the fluids pyrolysed in the oven. This fluid (nitrogen or helium) sweeps the sample by flowing through the piston. Distribution means (not shown) lead the carrier fluid to the upper part of the oven to perform a backflushing purge of the inside of the oven when the piston moves backward, for example at the end of the pyrolysis stage to transfer the sample and/or to load another sample. In fact, the influence of oxygen on the organic deposits on the walls of the pyrolysis oven can generate oxygen-containing compounds SOx likely to disturb the analysis.

A temperature probe 8 measures the temperature at the bottom of the boat, thus very close to the sample. The measuring point of another temperature probe 9 is in the wall of the oven, near to the upper position of the boat, a position corresponding to the optimum heating point. The temperature of the oven is preferably programmed by means of probe 8, which allows good control and knowledge of the sample pyrolysis temperature. Temperature probe 9 is used to control the temperature of oven 1 when the oven is open and piston 4 is lowered to extract boat 3 and replace it by another one. Thus, the temperature of oven 1 can be maintained at a value that is very close to the value determined for the next pyrolysis, which allows to prevent too high a thermal loss.

Heating set 1A is identical to heating set 1 in every respect. This set 1A is intended for oxidation of a sample, generally after pyrolysis. Identical elements are indexed "A". It can be noted that the fluid injected through line 7A is air in this case.

Heating sets 1 and 1A both have temperature regulation means allowing to program the temperature gradient, and the temperature can reach or even exceed 850° C.

Reference number 10 designates the flame ionization detector FID delivering a signal S representative of the amounts of hydrocarbon products released by the sample during heating. Arrow 11 represents the transfer of signal S to the digitizing means. The flame ionization detector FID must withstand high temperatures and therefore has to be fitted with joints withstanding these conditions without creeping or desorbing products likely to cause a baseline drift.

Its linearity and its sensitivity, associated with a very low baseline drift, guarantee a high-accuracy hydrocarbon analysis.

The analog signal will be digitized and smoothed with the maximum number of points which is a function of the programming rate.

Line 12 leads part of the stream to means 13 for continuous analysis of the amounts of $CO_2$ and of CO produced by pyrolysis of the sample. At the outlet of the pyrolysis oven, the divided stream is heated to at least 360° C. to prevent condensation of heavy products.

Line 12A leads at least part of the oxidation stream to means 13A for continuous analysis of the amounts of $SO_2$, CO and $CO_2$ produced.

Distribution means 14 allows to use only the CO and $CO_2$ analysis means for the stream from the pyrolysis oven. Distribution means 14A allows to use only the $SO_2$, CO and $CO_2$ analysis means. Preferably, for reasons of operating time gain, means 13A and 13 are assigned to a single heating means. The continuous analysis means are infrared detectors for example.

The first IR cell (13) can continuously measure the $CO_2$ and CO concentrations in the effluents during pyrolysis and oxidation. The second IR cell (13A) can continuously measure the $SO_2$, CO and $CO_2$ concentrations in the effluents during oxidation. The second cell gives access to new information such as the presence and the proportion of sulfur in the sample analysed, the maximum release temperatures, the shape of the peaks, the boundary between the mineral sulfur and the organic sulfur, and the distribution of the organic sulfur between a fraction referred to as labile and a fraction referred to as refractory.

The length of the cells of the detectors depends on the maximum sensitivity required, therefore on the minimum concentration to be measured. It depends on the amounts of $SO_2$, CO or $CO_2$ produced by the sample (therefore on its mass), on the analysis time (therefore on the heating conditions) and on the flow rate of the carrier gas which is a diluting factor.

The cell analysing the $SO_2$ measures maximum concentrations of 2000 ppm for a flow ranging between 50 and 300 ml. This range is linearized over the 0-2000 ppm concentration range.

The cell analysing the $CO_2$ measures maximum concentrations of 2% for a flow ranging between 50 and 300 ml. This range is linearized over four automatically changing ranges:

range 1: 0 to 2% $CO_2$
range 2: 0 to 1% $CO_2$
range 3: 0 to 0.5% $CO_2$
range 4: 0 to 0.25% $CO_2$ The cell analysing the CO measures maximum concentrations of 1% under the same conditions as cell $CO_2$. The 4 ranges are:

range 1: 0 to 1% CO
range 2: 0 to 0.5% CO
range 3: 0 to 0.25% CO
range 4: 0 to 0.125% CO The signals recovered on the IR cells are reshaped to obtain curves with the same attenuation, digitized as for the FID signal.

The device also comprises stream purification means 15 and 15A.

Arrows 16 and 16A show the transfer of the measurements to the electronic digitizing means.

Furthermore, the device comprises a sample changer 17 whose arm 18 is suited to displace the boat of a sample between three possible positions: pyrolysis oven, oxidation oven, holder 19.

The sample changer mechanics is simplified so that the displacements can be performed by stepping electric motors. Thus, all the control possibilities are given and they only depend on the operating software. It is possible, for example, to load the boats only in the oxidation oven for particular studies. Another particular application is the thermal treatment of samples in an oven and recovery thereof on boat support or holder (19) to analyse them according to the desired Rock-Eval cycle.

The boat support is not linear but circular: it has the shape of a carousel that occupies less room and allows to have faster access to the desired boat by means of a forward or reverse motion of the boat changer. A number allowing passage of the samples to be programmed not only in the chronological order of the position of the boats on the changer but also, either depending on the various types of cycles or analyses, or depending on analysis priorities, is assigned to each location.

Figure 2:
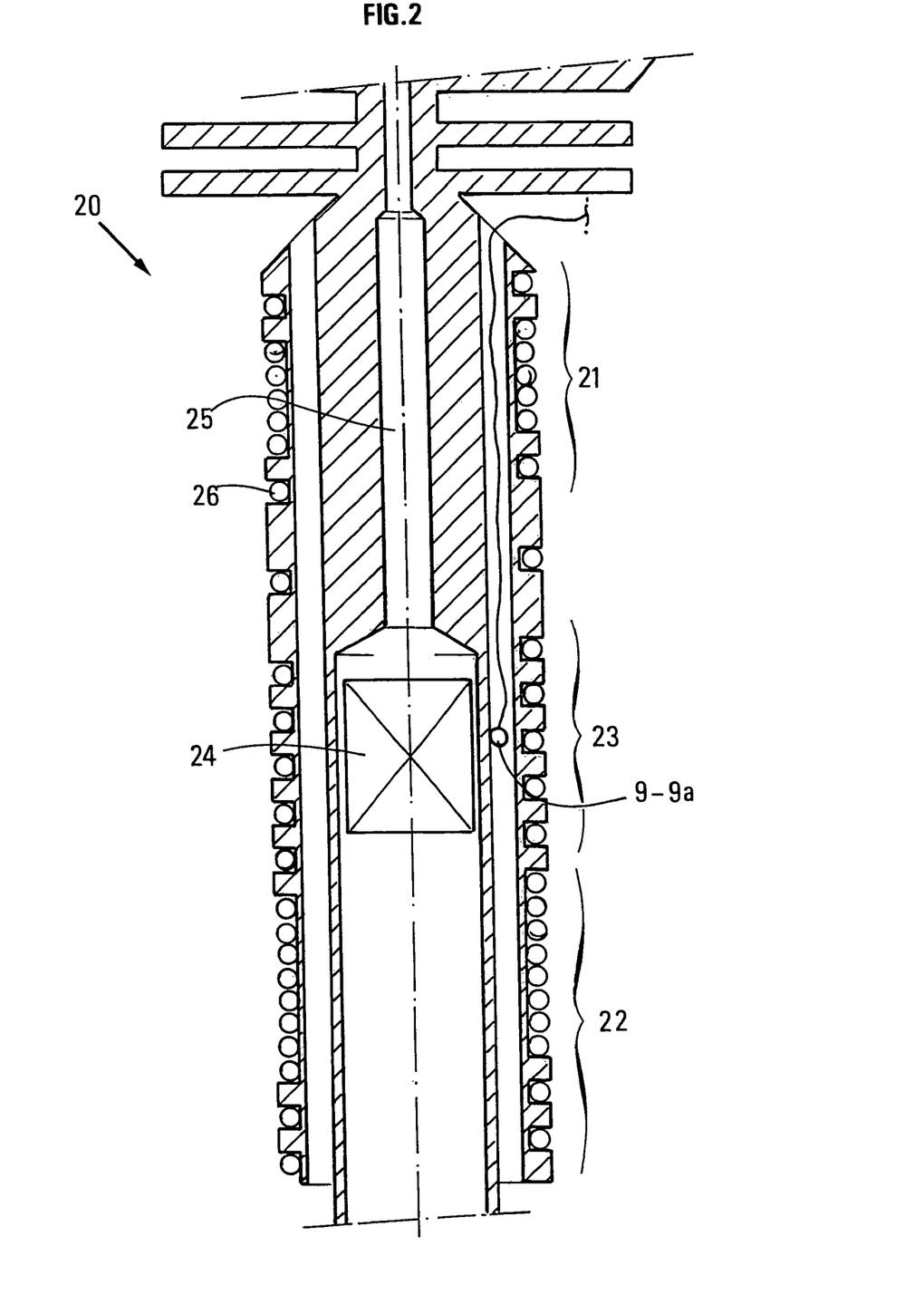
FIG. 2 shows the principle of the heating elements.

FIG. 2 shows the particular structure of the pyrolysis and oxidation ovens. Optimization of the heating elements is necessary to obtain temperatures at least above 850° C. and an initial temperature of at least 100° C., good linearity of the thermal gradients applied, energy savings and a temperature at the sample very close to the set temperature value.

Oven 20 has a tubular shape and comprises three main parts: two end parts 21 and 22, and a central part 23 where the sample is placed in testing position, according to the location diagrammatically shown by reference number 24.

The diameter of the inner space of the tube making up oven 20 is reduced 25 at the downstream end of the oven in relation to the direction of circulation of the stream carrying the pyrolysis or oxidation effluents. Winding of heating resistor 26 is optimized as follows: the resistor is mainly coiled with a closed winding in the two end parts 21 and 22 whereas, in central part 23, the winding pitch is larger, doubled for example. The resistor heats the body of the oven by contact, and contact can be improved by embedding the resistor in a metal alloy. The temperature measuring point of thermocouple 9 or 9A is placed as close as possible to the inner wall of the oven, near to location 24.

The ovens thus structured have the following advantageous characteristics:

The initial Ti and final Tf temperatures range between 100° C. and 900° C.

The heating program is multislope. It is possible to introduce one or more program segments between Ti and Tf that can be variable-duration isotherms or gradients whose rates range from 0.2° C./min to 50° C./min.

The reference during analysis being the temperature, beeps corresponding to well-determined temperatures are used to perform switching or connection operations. The temperature rise curve will be associated with all the analysis curves.

The thermal inertia and the required power being low, it is possible to lower initial temperature Ti and to facilitate cooling of the ovens for fast return to the initial temperature.

Volatilization of the lighter free hydrocarbons (below C5-C6) contained in a rock can thus be carried out at low temperature (approximately 100° C.). Then, separation of the components according to their boiling point is caused through suitable temperature programming. This technique can be applied to the study of either source rocks or of reservoir impregnations.

The possibility of carrying out a pyrolysis up to about 850° C. allows to obtain, particularly in the case of certain samples, complete volatilization or degradation of the residual organic matter contained in source rocks or reservoir rocks (C6 to C40 hydrocarbons and resins and asphaltenes). The petroleum potential of the sample is thus increased, in some cases, by a quite significant amount in relation to a conventional pyrolysis at 600° C., which gives a more representative IH.

Furthermore, the kinetic parameters of the organic matters of terrestrial origin, determined by means of the pyrolysis, are more precise when the adjustment pyrolysis curves come back to the baseline (case of the curves resulting from fast programming).

High-temperature pyrolysis is also useful for determining high maturities of the source rocks by means of the Tmax scale. A conventional pyrolysis up to 650° C. gives, in fact, in some cases of mature rocks, a peak S2 that only represents the cracking start without reaching the peak maximum. On the other hand, high-temperature pyrolysis allows to obtain temperatures Tmax above approximately 587° C. by means of a complete pyrolysis of the sample.

A programmed oxidation temperature that can reach 850° C. allows to burn the most resistant cokes. It is then possible to measure all of the organic carbon and sulfur, including the difficult case of very mature source rocks (case of highly evolved coals). The proportions of total organic sulfur (TOS) and of total organic carbon (TOC) are then quite comparable to the values obtained by means of the conventional elemental analysis.

High-temperature oxidation is necessary to decompose the minerals containing sulfur, notably pyrite and sulfates such as gypsum and bitter salt, which only degrade at temperatures above 600° C., for heating rates below 5° C./min. The total mineral sulfur (MOS) of the rocks and of the organic matters in which pyrite can be disseminated is thus obtained.

Figure 3A:
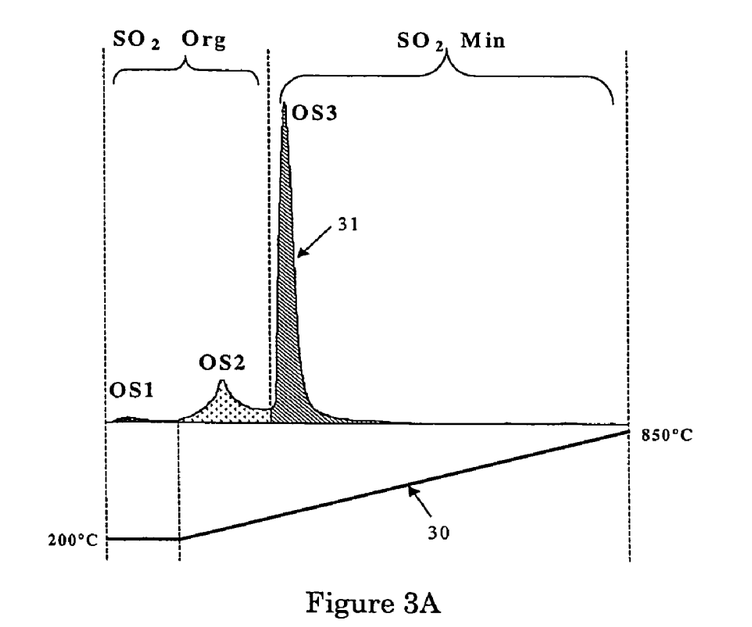
FIGS. 3A and 3B show records of the continuous $SO_2$ measurements obtained with the present device, FIG. 4 diagrammatically shows a petroleum evaluation set.
Figure 3B:
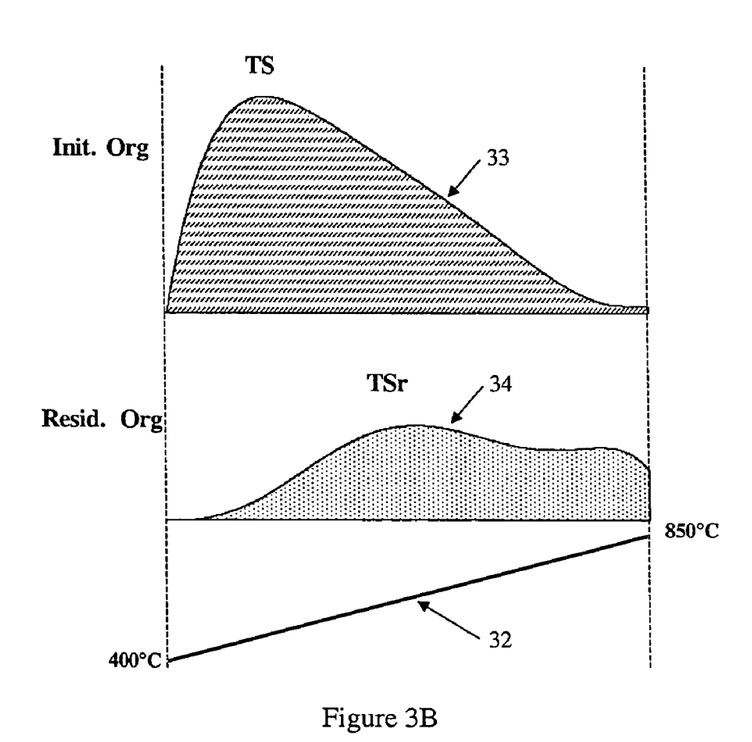

FIGS. 3A and 3B show type $SO_2$ measurements carried out with the device described in FIG. 1.

The graph of FIG. 3A relates to the continuous $SO_2$ measurement and recording during oxidation of a sample. The graphs of FIG. 3B relate to the continuous $SO_2$ measurement and recording during two oxidation operations of two aliquots of a sample: one directly oxidized, the other oxidized after pyrolysis in an inert atmosphere.

In FIG. 3A, curve 30 represents the oxidation temperature to which the sample was subjected. In the example given here, an isothermal stage is observed at 200° C., followed by a temperature rise according to a predetermined gradient, of the order of 10° C./min, a maximum temperature of 850° C. being reached at the end of the pyrolysis carried out in an oxidizing atmosphere.

Curve 31 represents the $SO_2$ signal continuously recorded by the IR cell. It comprises a first peak OS1 corresponding to the oxidation of the free hydrocarbons that volatilize during the isothermal stage, a second peak OS2 corresponding to the $SO_2$ produced by the combustion of the sulfur-containing organic constituents, a third peak OS3 corresponding to the $SO_2$ produced by the combustion of the sulfur-containing minerals, notably pyrite in this example. The proportion of total organic sulfur TOS is the sum of peaks OS1+OS2. The proportion of total mineral sulfur MOS is represented here by peak OS3.

In FIG. 3B, curve 32 represents the end of the oxidation temperature rise to which two aliquots of a single were subjected. Considering the nature of the sample tested, no peak appears while heating from 200 to 400° C. Curves 33 and 34 both correspond to the amount of $SO_2$ produced by each aliquot subjected to the temperature law of curve 32, similar to the law of FIG. 3A. Curves 33 and 34 are provided by continuous $SO_2$ measuring means, for example infrared detectors specifically suited to the present device.

Curve 33 defines a peak TS2 resulting from the combustion of the organic sulfur when the sample is directly heated in an oxidizing atmosphere. The $SO_2$ formed results both from the oxidation of the labile organic sulfur and of the refractory organic sulfur. Curve 34 defines a peak TSr resulting from the combustion of the organic sulfur when the sample is heated in two stages, first with a pyrolysis in an inert atmosphere, then in an oxidizing atmosphere. The $SO_2$ formed then results from the oxidation of the refractory organic sulfur alone. The ratio of the surface areas of curves 33 and 34 to the corresponding mass of the aliquot of the sample analysed thus allows to measure the proportions of labile organic sulfur and of refractory organic sulfur in the sample.

Figure 4:
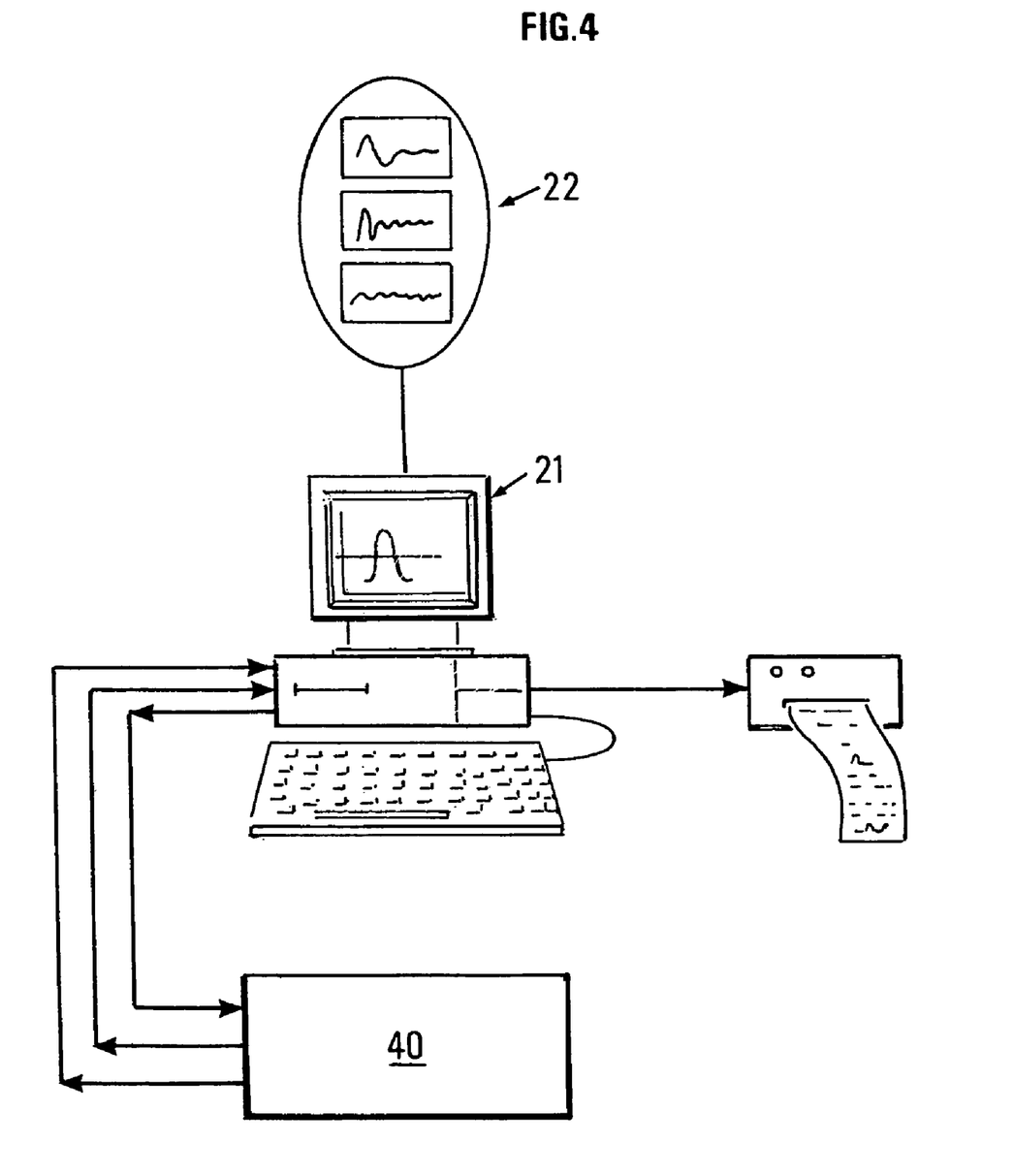

FIG. 4 shows the general architecture of the system allowing petroleum measurement and evaluation from a sample.

Reference number 40 designates the measuring automaton, the ovens and the various signal detectors as described in FIGS. 1 and 2. Reference number 21 represents a computer, of PC type for example, comprising a central processing unit and a display screen. The control and acquisition software is of WINDOWS type, thus allowing the user to readily select the desired type of analysis and cycle, and to monitor the progress of the analysis on a screen. Chart 22 symbolizes the various types of analysis that can be carried out by the type of automaton according to the present invention. The measuring set allows visual display and processing of the results during the acquisition of new measurements. The output of curves or of charts with the printer or their display on the screen, partial processing of the data and input or changes in the parameters of new analyses allow the operator to save a considerable amount of time.

The computer comprises several softwares managing several types of analysis, for example those mentioned hereafter, which are trade names registered by IFP:

ROCKSIX: acquisition of Rock-Eval data and determination of the true pyrolysis temperatures.

ROCKINT: interpretation of these data after correction and input of complementary information.

OPTKIN: determination of the kinetic parameters of the source rocks.

MATOIL: hydrocarbon maturation and generation model.

GENEX: hydrocarbon generation and expulsion model per carbon class.

The various analysis types depending on the category of the samples to be processed (raw rock, pure organic matters and kerogens, reservoir samples) or on the results necessary and useful to the operator are described in document EP-0,767,375.

The invention claimed is:

1. A method allowing determination of at least one petroleum characteristic of a geologic sediment sample, wherein each of the two parts of the sample is heated according to an oxidizing heating comprising being heated in an oxidizing atmosphere, its temperature being successively raised to a first, then to a second value, said first value being below 200° C. then maintained substantially constant for a certain time, said second value ranging between 600° C. and 850° C. being reached with a temperature gradient ranging between 1 and 30° C./min, from said first value, characterized in that the amount of $SO_2$ contained in the effluent resulting from said oxidizing heating is measured continuously, every moment of the heating period of said sample, and in that the following stages are carried out:

continuous measurement of the amount of $SO_2$ contained in the effluent resulting from said oxidizing heating of part of the sample previously subjected to a pyrolysis stage in an inert atmosphere, continuous measurement of the amount of $SO_2$ contained in the effluent resulting from said oxidizing heating of another part of the sample, not previously subjected to a pyrolysis stage in an inert atmosphere; and determining at least one petroleum characteristic of the sample by comparing the measurements of the amounts of $SO_2$.

2. A method as claimed in claim 1, wherein a curve representative of said $SO_2$ amount is drawn, and the $SO_2$ of organic origin is distinguished from the $SO_2$ of mineral origin from said continuous measurements and from the shape of the curve.

3. A method as claimed in claim 1, wherein labile organic sulfur is distinguished from refractory organic sulfur through combined interpretation of the measurements resulting from said stages.

4. A method as claimed in claim 1, wherein in said oxidized heating, the temperature of each of the two parts of the sample is raised to the first value by providing each of the two parts of the sample in a heating set having a temperature maintained at the first value.

5. A method for determining at least one petroleum characteristic of a geologic sediment sample, comprising:

providing first and second parts of a geologic sediment sample;

subjecting the first part of the sample to a pyrolysis stage in an inert atmosphere, and then heating the first part of the sample in an oxidizing atmosphere according to a heating program comprising successively raising a temperature of the first part of the sample to a first temperature of 200° C. or below, then maintaining the first part of the sample substantially constant at the first temperature for a certain time, then raising the temperature of the first part of the sample with a temperature gradient ranging between 1 and 30° C./min, from the first temperature to a second temperature ranging between 600° C. and 850° C.;

continuously measuring an amount of $SO_2$ contained in effluent resulting from heating the first part of the sample in the oxidizing atmosphere according to the heating program;

heating the second part of the sample in an oxidizing atmosphere according to the heating program comprising successively raising a temperature of the second part of the sample to the first temperature, then maintaining the second part of the sample substantially constant at the first temperature for a certain time, then raising the temperature of the second part of the sample with a temperature gradient ranging between 1 and 30° C./min, from the first temperature to the second temperature;

continuously measuring an amount of $SO_2$ contained in effluent resulting from heating the second part of the sample in the oxidizing atmosphere according to the heating program; and determining at least one petroleum characteristic of a geologic sediment sample by comparing the amount of $SO_2$ contained in effluent resulting from heating the first part of the sample in the oxidizing atmosphere according to the heating program with the amount of $SO_2$ contained in effluent resulting from heating the second part of the sample in the oxidizing atmosphere according to the heating program.

6. A method as claimed in claim 5, wherein successively raising a temperature of the first part of the sample to the first temperature comprises providing the first part of the sample in a heating set having a temperature maintained at the first temperature, and wherein successively raising a temperature of the second part of the sample to the first temperature comprises providing the second part of the sample in a heating set having a temperature maintained at the first temperature.

* * * * *